United States Patent

Redmore

[11] 4,163,850
[45] Aug. 7, 1979

[54] POLYCYCLIC FULL QUATERNARY NITROGEN-HETEROCYCLIC PHOSPHONATES

[75] Inventor: Derek Redmore, Ballwin, Mo.

[73] Assignee: Petrolite Corporation, St. Louis, Mo.

[21] Appl. No.: 860,820

[22] Filed: Dec. 15, 1977

Related U.S. Application Data

[60] Continuation of Ser. No. 380,605, Jul. 19, 1973, abandoned, which is a division of Ser. No. 117,082, Feb. 19, 1971, Pat. No. 3,770,750.

[51] Int. Cl.² ............................. C07F 9/60; C07F 9/62
[52] U.S. Cl. ..................................................... 546/21
[58] Field of Search ...................... 260/283 P, 286 Q; 546/21

[56] References Cited

U.S. PATENT DOCUMENTS

| | | | |
|---|---|---|---|
| 3,431,265 | 3/1969 | Wakeman et al. | 260/286 Q |
| 3,435,039 | 3/1969 | Wakeman et al. | 260/286 Q |
| 3,560,507 | 2/1971 | Wakeman et al. | 260/286 Q |
| 3,786,055 | 1/1974 | Redmore | 260/283 P |

OTHER PUBLICATIONS

Schwartz, et al., "Surface Active Agents and Detergents," vol. II, Interscience, pp. 210–215 (1958).

*Primary Examiner*—Donald G. Daus
*Assistant Examiner*—Diana G. Rivers
*Attorney, Agent, or Firm*—Sidney B. Ring; Hyman F. Glass

[57] ABSTRACT

Quaternary nitrogen-heterocyclic phosphonates wherein the phosphonate group is ortho- or para- to the nitrogen heterocyclic group, where the compounds are characterized as follows:

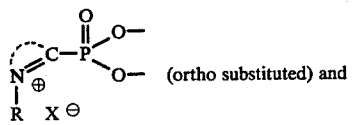

(ortho substituted) and

-continued

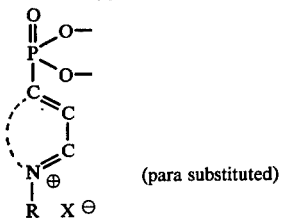 (para substituted)

wherein the dotted line represents a cyclic structure which cyclic structure may be the sole cyclic structure, or may be attached to other cyclic groups, where R is a hydrocarbon or a substituted hydrocarbon group such as alkyl, aryl, alkaryl, aralkyl, etc., and X is an anion such as halogen, a sulfite, a sulfate, a sulfonate-containing group, etc.

These nitrogen-heterocyclic phosphonates are prepared by reacting an aromatic nitrogen-heterocyclic compound, wherein the nitrogen atom is in the form of a quaternary alkoxy derivative (N—OR hereinafter defined) with a phosphite salt, preferably in the form of an ester of the phosphite, as exemplified by the following equation:

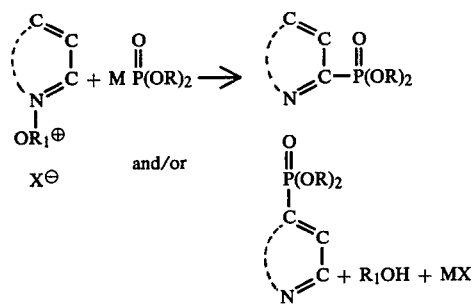

Quaternaries of these compounds are prepared by further reaction with a quaternizing agent.

These compounds which may be characterized as quaternaries of phosphonates of nitrogen-heterocyclics have many uses including their use as biocides, such as bacteriocides, herbicides, corrosion inhibitors and chelating agents.

7 Claims, No Drawings

POLYCYCLIC FULL QUATERNARY NITROGEN-HETEROCYCLIC PHOSPHONATES

This is a continuation of Ser. No. 380,605, filed July 19, 1973, and now abandoned, which in turn is a division of Ser. No. 117,082, filed Feb. 19, 1971, now U.S. Pat. No. 3,770,750, patented Nov. 6, 1973.

This invention relates to quaternaries of nitrogen-heterocyclic phosphonates. More particularly this invention relates to quaternaries of nitrogen-heterocyclic phosphonates wherein the phosphonate group is ortho or para to the heterocyclic nitrogen group. Still more particularly, this invention relates to compounds characterized by the following groups:

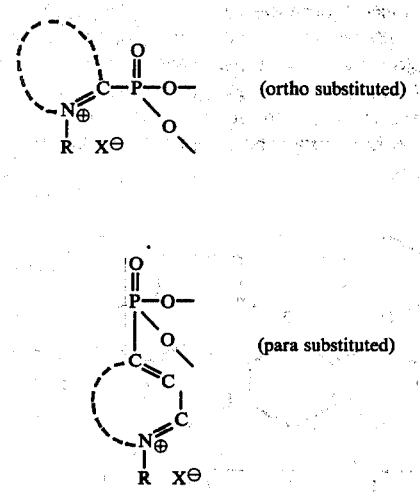

wherein the dotted lines indicate a cyclic structure, which cyclic structure may be the sole cyclic structure or may be attached to other cyclic groups. These compounds may be characterized as phosphonates of quaternary nitrogen-heterocyclics.

This invention also relates to the preparation of these quaternary phosphonates which comprises reacting an aromatic nitrogen-heterocyclic, wherein the nitrogen atom is in the form of a quaternary alkoxy derivative (N—OR), with a phosphite salt, preferably in the form of an ester of the phosphite, as exemplified by the following equation:

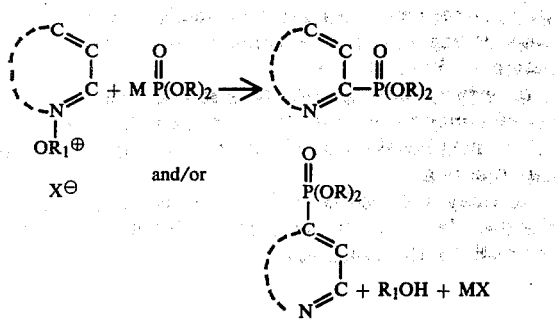

These products are then reacted with a quaternizing agent to yield the quaternaries of this invention as shown in the following equation:

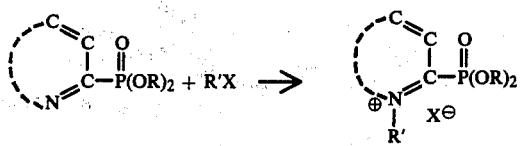

This invention also relates to uses for these quaternary compounds for example as biocides, such as bacteriocides, herebicides, corrosion inhibitors, chelating agents, etc.

In my application Ser. No. 733,328 filed May 31, 1968, now abandoned, there are described and claimed processes for preparing dihydro nitrogen-heterocyclic phosphonates and the resulting phosphonates which are substituted ortho and/or para to the heterocyclic-nitrogen atom, etc. For example, the invention of Ser. No. 733,328 may be illustrated by the following equations:

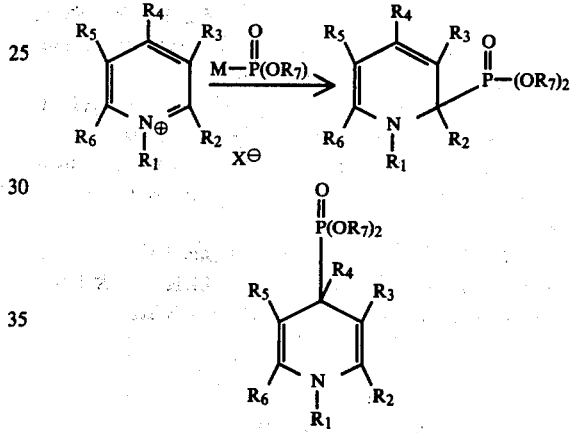

$R_1$, $R_2$, $R_3$, $R_4$, $R_5$, $R_6$ may be hydrogen or a substituted group, for example, alkyl, cycloalkyl, aryl, alkaryl, aralkyl, etc.

$R_7$ is an ester moiety for example alkyl, aryl, cycloalkyl, aralkyl, alkaryl, etc., oxyalkylated groups, etc.

The groups of $R_1$ to $R_7$ may also be further substituted provided the substituted groups do not interfere with the reaction.

X is any suitable anion, for example, halogen, e.g., chlorine, bromine, iodine, etc., —SO$_4$R″, —SO$_3$R″ where R″ is alkyl, etc., such as —SO$_4$Me, —SO$_4$Et,

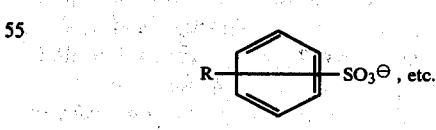

Application Ser. No. 801,856, filed Feb. 24, 1969, now U.S. Pat. No. 3,673,196, relates to a process of preparing analogous nitrogen heterocyclic phosphonates as contrasted to the dihydro-heterocyclic phosphonates of Ser. No. 733,328 (i.e., full heterocyclic as contrasted to dihydro-heterocyclic).

The products of Ser. No. 801,856 may be illustrated by the following equations:

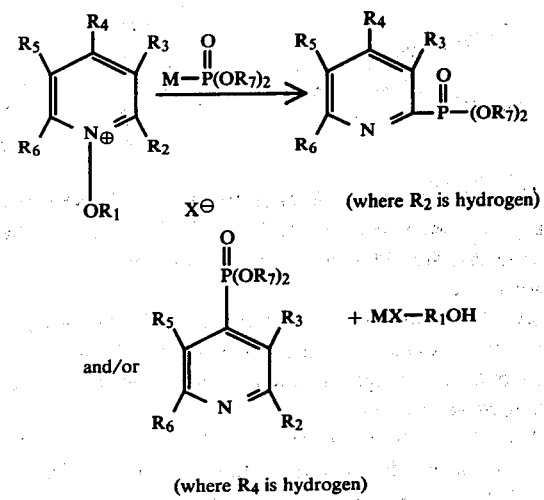

(where $R_2$ is hydrogen)

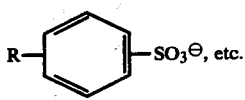

(where $R_4$ is hydrogen)

where $R_1$ is a hydrocarbon group such as alkyl, cycloalkyl, aryl, aralkyl, alkaryl, etc., $R_2$, $R_3$, $R_4$, $R_5$, $R_6$ is hydrogen or a substituted group, for example, alkyl, cycloalkyl, aryl, alkaryl, aralkyl, etc.

$R_7$ is an ester moiety for example alkyl, aryl, cycloalkyl, aralkyl, alkaryl, etc., oxyalkylated groups, etc.

The groups of $R_1$ to $R_7$ may also be further substituted provided the substituted groups do not interfere with the reaction.

X is any suitable anion, for example, halogen, e.g., chlorine, bromine, iodine, etc., $-SO_4R''$, $-SO_3R''$, where R'' is alkyl, such as $-SO_4Me$, $-SO_4Et$, R—⌬—$SO_3^\ominus$, etc.

It is to be noted that in the invention described in Ser. No. 733,328 the $R_1$ group remains affixed to the heterocyclic nitrogen throughout the reaction and in the final product, thus yielding a dihydro derivative of a heterocyclic compound; whereas in the present invention the nitrogen bonded $OR_1$ group is removed as an alcohol moiety during the reaction to yield the heterocyclic compound itself.

In preparing the compounds of Ser. No. 801,856 it is convenient to start with nitrogen-heterocyclic compound, oxidize it to the N-oxide, react this with an alkyl ester of an inorganic acid such as alkyl halide, alkyl sulfate, etc., to form the $OR_1$ group, and to then react the salt of a phosphite ester to yield the heterocyclic phosphonate as illustrated by the following series of reactions:

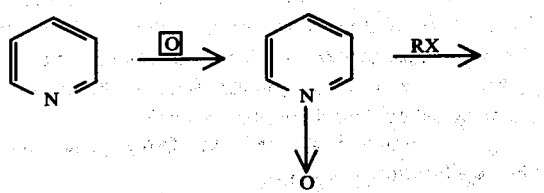

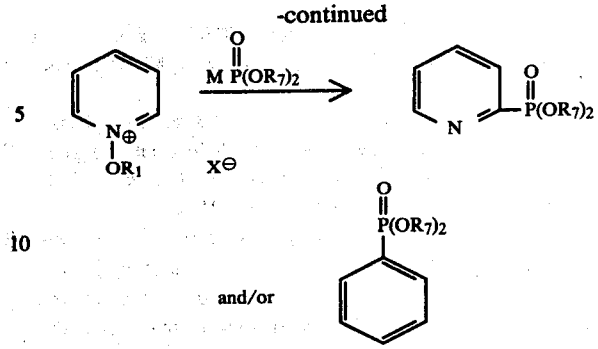

and/or

Any nitrogen heterocyclic having an available ortho and/or para position capable of being activated by quaternary formation of the nitrogen group with an $-OR_1$ group so as to promote reaction with salts of phosphite esters can be employed. This includes heterocyclics having one or more rings, where at least one ring has a nitrogen heterocyclic group and the other rings are carbocyclic or heterocyclic, i.e., they may contain oxygen or other non-carbon elements in the ring, etc., for example,

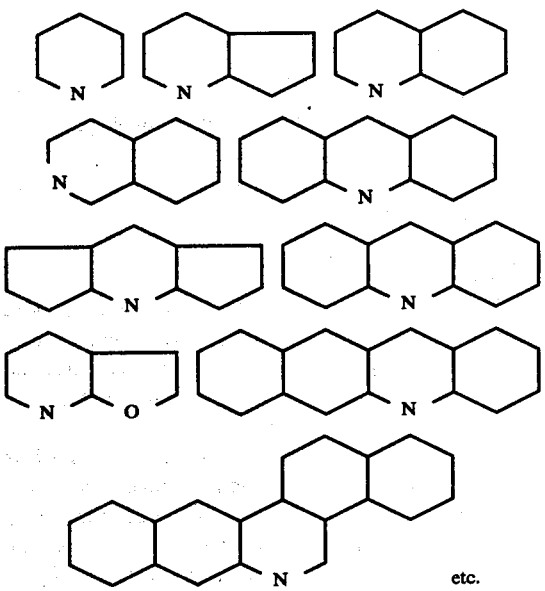

etc.

The above ring systems may also be substituted. The adjacent rings may also contain heterocyclic groups for example oxygen, nitrogen, etc., and/or may contain rings having less than six molecules in the ring, for example a 5 member ring.

In certain instances more than one nitrogen-heterocyclic ring may be capable of reacting with the phosphite salt so that phosphonate substitution may occur in more than one ring.

X is any suitable anion, for example, halogen, e.g., chlorine, bromine, iodine, etc., $-SO_4R''$, $-SO_3R''$ where R'' is alkyl such as

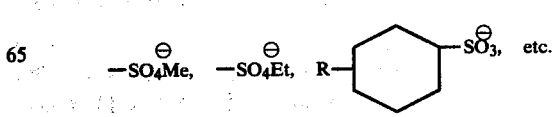

Representative examples of heterocyclic reactants include pyridines and benzo- and dibenzo- derivatives of pyridine, for example, pyridine, alkylated pyridines such as 2-picoline, 3-picoline, 4-picoline, etc., 2,4-lutidine, 2,6-lutidine, 2,3-lutidine, etc., collidines, etc., quinoline and alkylated quinolines, etc., isoquinolines, and alkylated isoquinolines, etc., phenanthridines, and substituted phenanthridines, etc., acridines and substituted acridines, etc.

The nitrogen group in the heterocyclic ring is reacted with a quaternizing agent to activate the ring.

The phosphorous-containing reactant is a metal salt of phosphorous acid, preferably in the form of an alkali metal salt in which the metal is directly bonded to phosphorous. In order to prevent undesirable side reactions the phosphorous acid is used in the form of a derivative, preferably as a diester.

Where the phosphite ester contains more than one phosphite unit, a plurality of heterocyclic units may be joined thereto, for example

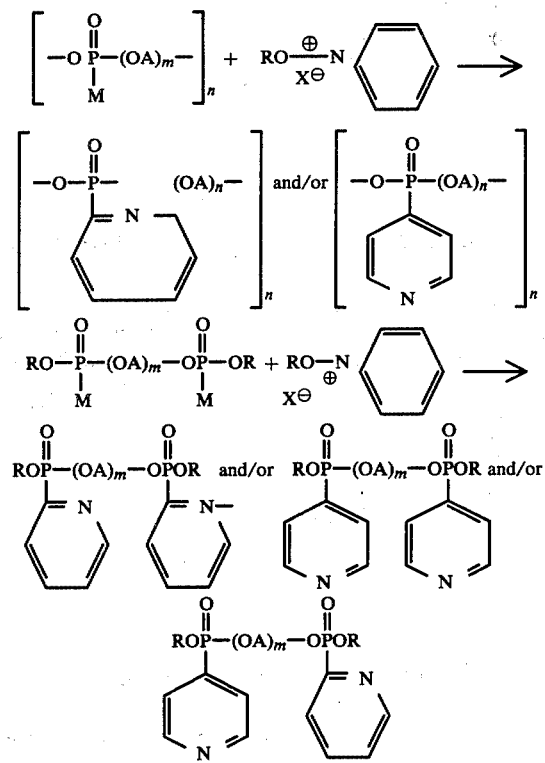

In general, the reaction is carried out in an inert solvent which is water free at a temperature and time sufficient to promote the desired reaction. Ether solvents such as diethyl ether, dioxane and tetrahydrofuran are useful, as well as aromatic hydrocarbon solvent like benzene, toluene, etc. Particularly useful are dipolar aprotic solvents such as dimethyl sulfoxide, dimethyl formamide N-methyl pyrrolidone. Combinations of these various types of solvents can also be advantageously used. Temperature and time are interrelated. Thus, a temperature of from 30° to the decomposition temperature of reactants and products can be employed, the upper limit of temperature being generally about 150° C., for a time of from 0.5–10 hours, but preferably 1–3 hours. The inorganic salt is separated from the organic layer by filtration or by water extraction and the phosphonate derivative is separated from the organic layer. In addition the reaction is best carried out on an inert atmosphere such as nitrogen, argon, etc. In this way the attack of oxygen on phosphite salts and on the products is prevented.

The following examples are presented by way of illustration and not of limitation.

EXAMPLE 1

Diethyl Pyridine 2-phosphonate

To pyridine N-oxide (19 g; 0.2 mole) was added dimethyl sulfate (25.2 g; 0.2 mole) during 30 minutes. The reaction was completed by heating at 100° C. for two hours yielding N-methoxy pyridinium methosulfate. Diethyl sodio phosphonate was prepared by dissolving sodium (4.6 g; 0.2 mole) in a solution of diethyl phosphite (27.6 g; 0.2 mole) in dioxane (100 ml) in an argon atmosphere. The N-methoxy pyridinium quaternary was suspended in toluene by stirring while the diethyl sodio phosphonate solution was added. The reaction flask was cooled to maintain the temperature at 25°–35° C. After stirring for 1½ hours, water (100 ml) was added and the organic product isolated by chloroform extraction. Evaporation of the chloroform extract and distillation yielded diethyl pyridine-2-phosphonate with a small amount of diethyl pyridine 4-phosphonate. Yield — 14g (33%) bp 140°–8° C./1.5 mm. The presence of the two isomers was established by infrared absorption; 2-isomer 13.3 $\mu$ (strong, 4 adjacent hydrogen) and 4 isomer, 12.3 $\mu$ (weak, 2 adjacent hydrogen).

EXAMPLE 2

Diethyl 4-methyl Pyridine-2-Phosphonate

N-methoxy-4-methyl pyridinium methosulfate was prepared from 4-picoline-N-oxide (54.4g; 0.5 mole) and dimethyl sulfate (63g; 0.5 mole) and suspended by stirring with toluene (250 ml). To this suspension was added diethyl sodio phosphonate in dioxane (150 ml) prepared from diethyl phosphite (69g; 0.5 mole) and sodium (11.5g; 0.5 mole). This addition was carried out in 40 minutes during which time the temperature was controlled at 45° C. by cooling. After stirring for one hour, water was added to the reaction and the product isolated by chloroform extraction. Evaporation and distillation yielded diethyl 4-methyl pyridine-2-phosphonate 17g; bp 109°–112° 0.05 mm. The infrared spectrum shows absorption at 7.97 $\mu$ (P=O), 9.8 $\mu$ and 10.4 $\mu$ (P—O—C).

EXAMPLE 3

Diethyl Quinoline-2-Phosphonate and -4-Phosphonate

N-methoxyquinolinium methosulfate was prepared from quinoline N-oxide (50g; 0.344 mole) and dimethyl sulfate (43.5g; 0.344 mole). To this quaternary was added diethyl sodiophosphonate from diethyl phosphite (47.5g; 0.344 mole) and sodium (7.9g; 0.344 mole) in dioxane (100 ml.). The reaction was completed by heating at 100°–110° C. for two hours. Water was added to the reaction, after cooling, and the product was isolated by benzene extraction. Evaporation of the solvent and heating under vacuum at 140° C./2 mm gave a residue which was a mixture of diethyl quinoline 2-phosphonate and 4-phosphonate. Analysis found N = 5.4% calculated N. 5.28%.

EXAMPLE 4

Diethyl Isoquinoline-1-Phosphonate

N-methoxy isoquinolinium methosulfate was converted by reaction with diethyl sodio phosphonate in dioxane into diethyl isoquinoline-1-phosphonate in 30% yield using the procedure of Example 3. The product was purified by distillation bp 135°–140° C./0.15 mm.

EXAMPLE 5

Diethyl 4-Cyanopyridine-2-Phosphonate 4-cyano pyridine N-oxide was converted into its N-methoxy pyridinium salt with dimethyl sulfate and reacted in dioxane with diethyl sodio phosphonate by heating at 80°–85° C. for one hour. After cooling, water was added and the product isolated by chloroform extraction. Removal of unreacted reactants under vacuum left the slightly impure diethyl 4-cyano pyridine-2-phosphonate (70%). The infrared spectrum showed absorption at 4.5 $\mu$ (C≡N), 7.95 $\mu$ (P=O), 9.8 $\mu$ (P—O—C).

EXAMPLE 6

4-Methyl Pyridine-2-Phosphonic Acid

Diethyl 4-methyl pyridine-2-phosphonate (11g.). (The product from Example 2) was heated for six hours with 18% hydrochloric acid (120 ml) at 100°. The acid was removed under vacuum to leave a gum which was dissolved in ethyl alcohol. Addition of ether yielded white crystals which after drying gave pure 4-methyl pyridine 2-phosphonic acid (7.2g; 86) mp 272.6° C.

Analysis calculated: C, 41.62; H, 5.78; N, 8.09; P, 17.92%. Found: C, 41.65; H, 4.63; H, 8.09; P, 16.95%.

EXAMPLE 7

Quinoline 2- and -4-Phosphonic Acids

The product of Example 3 (7.7g) was heated under reflux for 3½ hours with 18% hydrochloric acid (60 ml.). Using the isolation procedure of Example 6 a crude quinoline phosphonic acid 5g. (82%) was isolated. Crystallization from acetic acid gave pure quinoline-2-phosphonic acid mp 200° C.

Analysis Calculated: N, 6.70%; P, 14.83%. Found: N, 6.33%; P, 14.71%.

With the above examples as illustrative examples, one can then react any of the nitrogen-heterocyclic phosphonates of Ser. No. 801,856 to yield the corresponding quaternaries. The resulting compounds will correspond to those of Ser. No. 801,856 except that the cyclic nitrogen is quaternized.

Thus, the ring will contain the following group

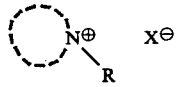

the rest of the molecule being unchanged.

Thus, the present invention relates to the reaction of the nitrogen-heterocyclic phosphates of Ser. No. 801,856 with quaternizing agents to form the corresponding quaternary compounds.

In general these quaternaries are prepared by carrying out the reaction under suitable conditions. For example, the nitrogen-heterocyclic phosphate either per se or dissolved in a suitable solvent and at least a stoichiometric amount of the quaternizing agent are mixed and the reaction mixture heated at a temperature and time sufficient to yield the quaternary product, for example, at about 60° C. to the decomposition point of reactants and products, such as from about 60° to 175° C. or higher, for example from about 80° to 150° C. for a period of from about one to 24 hours, such as from about 3 to 10 hours, but preferably about 4 to 6 hours. A convenient method of reaction is to dissolve the reactants in a suitable solvent and heat a reflux until quaternization is effected.

The following examples are presented by way of illustration.

EXAMPLE 1

Diethyl Pyridine-2 phosphonate Methoiodide

Diethyl pyridine-2-phosphonate (2g) was heated under reflux with methyl iodide (4.5g) in ethanol (20 ml) for 4 hours. Evaporation of the solvent and excess methyl iodide gave the pyridinium methiodide as a colorless oil which was readily water soluble. The structure of the product is:

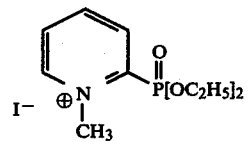

EXAMPLE 2

Diethyl Pyridine-2-Phosphonate Methyl Quaternary Methosulfate

Diethyl pyridine-2-phosphonate (4.3g) was heated under reflux in ethanol (30 ml) with dimethyl sulfate (2.5g) for 5 hours. Removal of solvent yielded the pure quaternary as an oil represented by the structure:

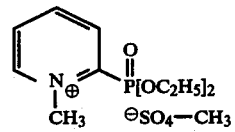

EXAMPLE 3

N-propyl Quaternary of Diethyl Pyridine-2-phosphonate

Diethyl pyridine-2-phosphonate (4.3g) was heated under reflux in ethanol (30 ml) with N-propyl iodide (3.6g) for 5 hours. Evaporation of the solvent gave the N-propyl-quaternary iodide as an oil represented as follows:

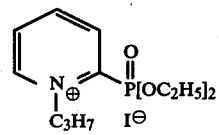

EXAMPLE 4

Quaternary from 1-Bromododecane and Diethyl Pyridine-2-Phosphonate

Diethyl pyridine-2-phosphonate (4g) and 1-bromododecane (4.65g) were heated at 140°–150° for 6 hours without solvent to effect quaternization. The product is represented as follows:

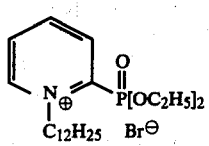

Other nitrogen-heterocyclic phosphonates prepared in Ser. No. 801,856 are similarly quaternized.

In order to save repetitive detail, the results are presented in tabular form:

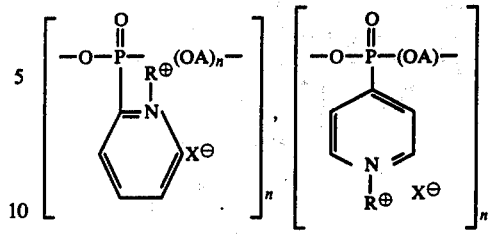

| Ex. | Nitrogen Heterocyclic Phosphonate | Quaternizing Agent | Quaternary Product |
|---|---|---|---|
| 5. | pyridine-P(OC$_2$H$_5$)$_2$ | (C$_2$H$_5$O)$_2$SO$_2$ | N-C$_2$H$_5$ pyridinium-P(OC$_2$H$_5$)$_2$, C$_2$H$_5$SO$_4^\ominus$ |
| 6. | 6-CH$_3$-pyridine-P(OC$_2$H$_5$)$_2$ | CH$_3$I | 6-CH$_3$-N-CH$_3$ pyridinium-P(OC$_2$H$_5$)$_2$, I$^\ominus$ |
| 7. | 4-CH$_3$-pyridine-P(OC$_2$H$_5$)$_2$ | CH$_3$I | 4-CH$_3$-N-CH$_3$ pyridinium-P(OC$_2$H$_5$)$_2$, I$^\ominus$ |
| 8. | pyridine-P(OC$_4$H$_9$)$_2$ | (CH$_3$O)$_2$SO$_2$ | N-CH$_3$ pyridinium-P(OC$_4$H$_9$)$_2$, SO$_4$CH$_3^\ominus$ |
| 9. | 4-CH$_3$-pyridine-P(OC$_2$H$_5$)$_2$ | C$_{12}$H$_{25}$Br | 4-CH$_3$-N-C$_{12}$H$_{25}$ pyridinium-P(OC$_2$H$_5$)$_2$, Br$^\ominus$ |
| 10. | quinoline-P(OC$_2$H$_5$)$_2$ | C$_{12}$H$_{25}$Br | N-C$_{12}$H$_{25}$ quinolinium-P(OC$_2$H$_5$)$_2$, Br$^\ominus$ |
| 11. | isoquinoline-P(OC$_2$H$_5$)$_2$ | C$_{12}$H$_{25}$Br | N-C$_{12}$H$_{25}$ isoquinolinium-P(OC$_2$H$_5$)$_2$, Br$^\ominus$ |

Where the phosphite ester contains more than one heterocyclic unit, corresponding polyquaternaries will be formed, for example,

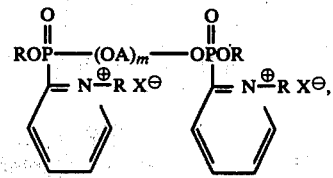

-continued

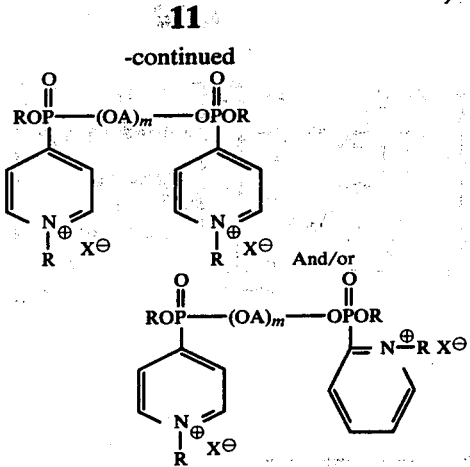

In addition, mono-heterocyclics can be reacted with polyquaternizing agent as a diquaternizing agent to yield diquaternaries, for example:

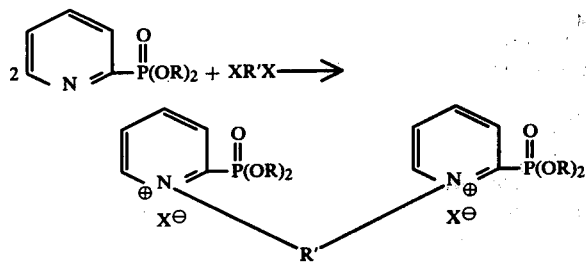

where R' is for example alkylene, cycloalkylene, arylene, alkarylenealkyl, dialkylether, alkenylene, alkynylene, etc., for example where R' is

| | |
|---|---|
| —(CH$_2$)— <br> 1-10 | or branched derivatives thereof, <br> or substituted derivatives thereof, <br> or substituted derivatives thereof, |
| ⟨phenylene⟩ | or substituted derivatives thereof, |
| ⟨thiophene-S⟩ | or substituted derivatives thereof, |
| —CH$_2$—⟨phenylene⟩—CH$_2$— | or substituted derivatives thereof, |
| —CH$_2$CH$_2$O—CH$_2$CH$_2$—, <br> —CH$_2$CH=CH—CH$_2$— <br> —CH$_2$C≡C—CH$_2$—, etc. | |

Corresponding diquaternaries of other heterocyclics can also be prepared, for example,

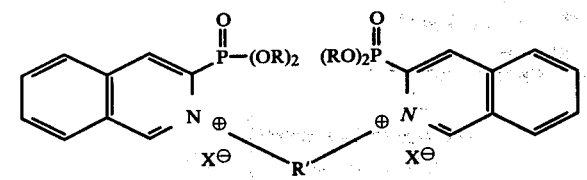

As is quite evident, other quaternary nitrogen-heterocyclic phosphonates are useful in my invention. It is, therefore, not only impossible to attempt a comprehensive catalogue of such compounds, but to attempt to describe the invention in its broader aspects in terms of specific quaternary nitrogen-heterocyclic phosphonates would be too voluminous and unnecessary since one skilled in the art could by following the description of the invention herein select a useful quaternary. This invention lies in the reaction of suitable quaternaries and their individual compositions are important only in the sense that they react to form useful products. To precisely define each specific useful quaternary in light of the present disclosure would merely call for chemical knowledge within the skill of the art in a manner analogous to a mechanical engineer who prescribes in the construction of a machine the proper materials and the proper dimensions thereof. From the description in this specification and with the knowledge of a chemist, one will know or deduce with confidence the applicability of specific quaternaries suitable for this invention. In analogy to the case of a machine, wherein the use of certain materials of construction or dimensions of parts would lead to no practical useful result, various materials will be rejected as inapplicable where others would be operative. I can obviously assume that no one will wish to use a useless quaternary nor will be misled because it is possible to misapply the teachings of the present disclosure to do so. Similarly, any quaternary nitrogen-heterocyclic phosphonate which is within the scope of this invention and effective as a biocide (as hereinafter stated) is within the scope of this invention.

I. WATER TREATMENT

This phase of the present invention relates to the treatment of water. More particularly, it is directed to providing improved means for controlling microbiological organisms including bacteria, fungi, algae, protozoa and other microbiological organisms which, if uncontrolled, multiply under certain conditions so as to present many serious problems. For example, in swimming pools the growth of these microbiological organisms is very desirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air-conditioning systems, on the farm and ranch, in the factory, in civilian and military hospitals and dispensaries, in camps, for swimming pools, baths and aquaria, waterworks, wells, reservoirs, by fire-fighting agencies, on maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bactericidal, fungicidal and algicidal. They further provide a simple process whereby water supplies, for whatever purposes intended, are rendered bacteriostatic, fungistatic and algistatic, i.e., said water supplies treated by the process of this invention will resist and inhibit the further growth or proliferation of bacteria, fungi, algae and all forms of microbial life therein.

II. WATER FLOODING IN SECONDARY RECOVERY OF OIL

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding takes place in the presence of sulfate-reducing bacteria.

Water flooding is widely used in the petroleum industry to effect secondary recovery of oil. By employing this process the yield of oil from a given field may be increased beyond the 20 - 30 percent of the oil in a producing formation that is usually recovered in the primary process. In flooding operations, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirable in carrying out this process to maintain a high rate of water injection with a minimum expenditure of energy. Any impediment to the free entry of water into oil bearing formations seriously reduces the efficiency of the recovery operation.

The term "flood water" as herein employed is any water injected into oil-bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Pore-plugging increases the pressure necessary to drive a given volume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

Organisms of the Desulfovibrio genus, more commonly known as sulfate reducing bacteria, are known particularly to preclude efficient operation of oil recovery by conventional water flooding techniques by producing $H_2S$ which reacts with iron or iron salts to precipitate black ferrous sulfide. These organisms are resistant to the effects of many known antimicrobial compounds.

III. HYDROCARBON TREATMENT

This phase of the present invention relates to the use of quaternaries as biocides in hydrocarbon systems.

In addition to being used as biocides in aqueous systems, the quaternary compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, $H_2S$, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

IV. MICROBIOCIDAL TESTING

The procedure was carried out in the following manner. Solutions of test compounds were aseptically added to a sterile broth which would support growth of the following test organisms
(1) Aerobic bacteria
(2) Sulfate reducing bacteria
to a concentration of 500 ppm by weight of broth. Growth media prescribed by the American Petroleum Institute were used. The broth containing the test compound was then dispersed into sterile disposable tubes and the tubes were innoculated with the growing organisms and incubated at 35° C. for 24 hours. The absence or presence of growth of microorganisms was determined by visual inspection with the following test compounds.

Ex. 2

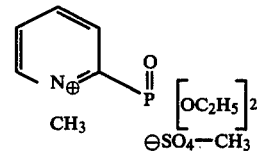

Ex. 3

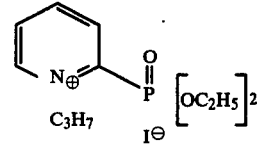

Ex. 4

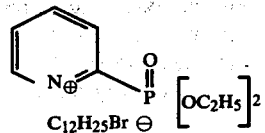

In contrast to the corresponding unquaternized compounds which showed no activity, the above compounds were active as biocides or biostats.

Having thus described my invention, what I claim is new and desire to obtain by Letters Patent is:

1. A full quaternary nitrogen-heterocyclic phosphonate selected from the group consisting of

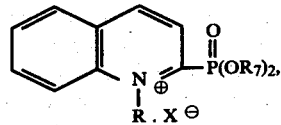 (1)

a mixture of (1) and 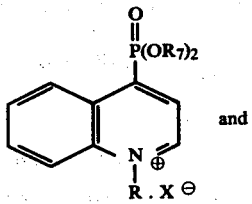 and (2)

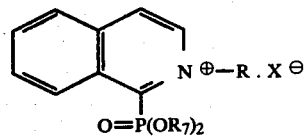 (3)

where R and $R_7$ are each alkyl and X is an anion.

2. The full quaternary nitrogen-heterocyclic phosphonate compound of claim 1 having formula (1).

3. The full quaternary nitrogen-heterocyclic phosphonate compound of claim 1 having the formula (3).

4. The full quaternary nitrogen-heterocyclic phosphonate of claim 1 which is the mixture (2).

5. The full quaternary nitrogen-heterocyclic phosphonate of claim 1 where X is selected from the group consisting of chlorine, bromine, iodine, $-SO_4R''$ and $-SO_3R''$, where $R''$ is alkyl.

6. The full quaternary nitrogen-heterocyclic phosphonate compound of claim 1 having the formula

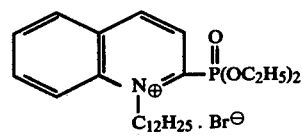

7. The full quaternary nitrogen-heterocyclic phosphonate of claim 1 having the formula

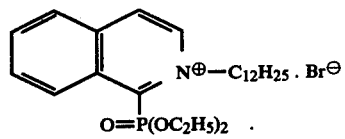

* * * * *